(12) United States Patent
Inukai et al.

(10) Patent No.: US 11,324,920 B2
(45) Date of Patent: May 10, 2022

(54) CATHETER

(71) Applicant: TERUMO KABUSHIKI KAISHA, Tokyo (JP)

(72) Inventors: Takito Inukai, Fujinomiya (JP); Yuya Otake, Fujinomiya (JP); Mariko Maruyama, Newark, DE (US); Kouta Hamuro, Fujinomiya (JP); Mitsuteru Yasunaga, Fujinomiya (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 303 days.

(21) Appl. No.: 16/291,182

(22) Filed: Mar. 4, 2019

(65) Prior Publication Data
US 2019/0192812 A1 Jun. 27, 2019

Related U.S. Application Data (63) Continuation of application No. PCT/JP2017/031133, filed on Aug. 30, 2017.

(30) Foreign Application Priority Data

Sep. 5, 2016 (JP) .............................. JP2016-172470

(51) Int. Cl.
*A61M 25/00* (2006.01)
*A61L 29/02* (2006.01)
*A61M 25/01* (2006.01)

(52) U.S. Cl.
CPC ............ *A61M 25/005* (2013.01); *A61L 29/02* (2013.01); *A61M 25/00* (2013.01);
(Continued)

(58) Field of Classification Search
CPC ............ A61M 25/005; A61M 25/0052; A61M 25/0053; A61M 25/0054; A61M 2025/0081
See application file for complete search history.

(56) References Cited

U.S. PATENT DOCUMENTS 4,636,346 A * 1/1987 Gold .................. A61M 25/001
138/109
4,863,442 A * 9/1989 DeMello ............... A61L 29/041
604/527

(Continued)

FOREIGN PATENT DOCUMENTS

EP 1 721 631 A1 11/2006
JP H6086822 A 3/1994
(Continued)

OTHER PUBLICATIONS

International Search Report (PCT/ISA/210) and Written Opinion (PCT/ISA/237) dated Nov. 7, 2017, by the Japanese Patent Office as the International Searching Authority for International Application No. PCT/JP2017/031133.

(Continued)

*Primary Examiner* — William R Carpenter
(74) *Attorney, Agent, or Firm* — Buchanan Ingersoll & Rooney PC (57) ABSTRACT

A catheter is disclosed having a distal end portion of a shaft with high breaking strength even if a wall thickness of the distal end portion of the shaft is relatively small. The catheter includes an elongated tube shaped shaft. The shaft has an inner layer having a lumen along a longitudinal direction, an outer layer covering an outer peripheral side of the inner layer, and a reinforcement body disposed on the outer peripheral side of the inner layer. The outer layer has a distal outer layer on a distal end portion of the shaft, an intermediate outer layer proximal to the distal outer layer, and a proximal outer layer proximal to the intermediate outer layer. The intermediate outer layer is more flexible and thicker than the proximal outer layer, and a distal end of the reinforcement body is located proximal to a distal end of the intermediate outer layer.

20 Claims, 4 Drawing Sheets

(52) U.S. Cl.
CPC .... *A61M 25/0045* (2013.01); *A61M 25/0108* (2013.01); *A61M 2025/0059* (2013.01)

(56) References Cited

U.S. PATENT DOCUMENTS

| | | | | |
|---|---|---|---|---|
| 5,221,270 | A * | 6/1993 | Parker | A61M 25/0045 604/264 |
| 5,234,416 | A * | 8/1993 | Macaulay | A61M 25/008 600/435 |
| 5,279,596 | A * | 1/1994 | Castaneda | A61M 25/005 138/133 |
| 5,308,342 | A * | 5/1994 | Sepetka | A61M 25/0054 604/525 |
| 5,658,263 | A * | 8/1997 | Dang | A61M 25/0041 604/264 |
| 5,676,659 | A * | 10/1997 | McGurk | A61M 25/0012 138/124 |
| 5,911,715 | A * | 6/1999 | Berg | A61M 25/0043 604/525 |
| 6,036,682 | A * | 3/2000 | Lange | A61M 25/0108 604/264 |
| 6,077,258 | A | 6/2000 | Lange et al. | |
| 6,106,510 | A * | 8/2000 | Lunn | A61M 25/0012 600/433 |
| 9,480,589 | B2 * | 11/2016 | Breyer | A61F 2/966 |
| 9,545,496 | B2 | 1/2017 | Hiroshige et al. | |
| 9,999,749 | B2 | 6/2018 | Hiroshige et al. | |
| 2005/0070880 | A1 | 3/2005 | Varma et al. | |
| 2007/0149927 | A1 | 6/2007 | Itou et al. | |
| 2008/0125752 | A1 * | 5/2008 | Gunderson | A61M 25/005 604/527 |
| 2010/0030165 | A1 * | 2/2010 | Takagi | A61M 25/0054 604/265 |
| 2017/0000973 | A1 * | 1/2017 | Otake | A61M 25/005 |

FOREIGN PATENT DOCUMENTS

| | | |
|---|---|---|
| JP | H10043300 A | 2/1998 |
| JP | 2009022432 A | 2/2009 |
| WO | 2005/056100 A1 | 6/2005 |
| WO | 2007013545 A1 | 2/2007 |
| WO | 2014045703 A1 | 3/2014 |

OTHER PUBLICATIONS

An English Translation of the International Search Report (Form PCT/ISA/210) and the Written Opinion of the International Searching Authority (Form PCT/ISA/237) dated Nov. 7, 2017, by the Japanese Patent Office in corresponding International Application No. PCT/JP2017/031133. (7 pages).

The extended European Search Report dated Apr. 24, 2020, by the European Patent Office in corresponding European Patent Application No. 17846558.9-1132. (5 pages).

\* cited by examiner

CATHETER

CROSS-REFERENCES TO RELATED APPLICATIONS

This application is a continuation of International Application No. PCT/JP2017/031133 filed on Aug. 30, 2017, which claims priority to Japanese Application No. 2016-172470 filed on Sep. 5, 2016, the entire content of both of which is incorporated herein by reference.

TECHNICAL FIELD

The present disclosure generally relates to a catheter to be inserted into a biological lumen.

BACKGROUND DISCUSSION

A treatment catheter is widely used for diagnosis or treatment in a biological lumen. The treatment catheter includes, for example, a balloon catheter used for percutaneous transluminal coronary angioplasty (PTCA).

A guiding catheter is inserted into the biological lumen in advance before the treatment catheter is inserted. The treatment catheter is inserted through a lumen of the guiding catheter. Recently, a technique (TRI: Trans Radial Intervention) is increasing in which the guiding catheter is inserted through an artery of an arm, particularly through a radial artery or brachial artery in the treatment of blood vessels of the lower extremity.

Since an elongated shaft of the guiding catheter used for TRI technique needs to be inserted into a radial artery having a small diameter, the outer diameter of the shaft needs to be as small as possible. In order to insert the treatment catheter through the lumen of the guiding catheter, the inner diameter of the shaft needs to be as large as possible. Therefore, a wall thickness of the shaft of the guiding catheter used for TRI technique needs to be relatively small.

In the catheter, a reinforcement body may be provided in the shaft in order to secure sufficient strength even if the wall thickness of the shaft is relatively small. Generally, the reinforcement body is generally a product obtained by weaving metallic wires. Examples of the catheter having a reinforcement body, for example, are disclosed in JP-A-10-43300.

Generally, when the wall thickness of the shaft is reduced, breaking strength against tensile load of the shaft is reduced. In a case of the shaft having a reinforcement body, breaking tends to occur in the end portion of the reinforcement body because the wall thickness of the shaft is the thinnest in the end portion of the reinforcement body. The shaft tends to be the starting point of elongation caused by tension, and the stress concentrates. Moreover, the presence of an edge in the end portion of the reinforcement body is also cited as a reason that the shaft tends to be the starting point of the breaking.

Therefore, even if the wall thickness of the shaft is relatively small, a distal end portion of the shaft including the end portion of the reinforcement body is required to have a relatively high breaking strength.

SUMMARY

A catheter is disclosed having a distal end portion of a shaft with a relatively high breaking strength even if the wall thickness of the distal end portion of the shaft is relatively small.

A catheter according to the present disclosure includes an elongated tube shaped shaft, in which the shaft has an inner layer having a lumen along a length direction, an outer layer covering an outer peripheral side of the inner layer, and a reinforcement body disposed on the outer peripheral side of the inner layer, the outer layer has a distal outer layer of a distal end portion of the shaft, an intermediate outer layer more proximal than the distal outer layer, and a proximal outer layer (or base outer layer) more proximal than the intermediate outer layer, and the intermediate outer layer is more flexible and thicker than the proximal outer layer (or base outer layer), and a distal end of the reinforcement body is located more proximal than a distal end of the intermediate outer layer.

In accordance with an exemplary embodiment, with the catheter configured as described above, it is possible to increase the breaking strength of the distal end portion of the flexible shaft while suppressing the occurrence of the stress concentration in the distal end of the reinforcement body when the shaft is pulled.

The reinforcement body includes metallic wires woven into a mesh shape, and distal end portions of the wires located at the distal end of the reinforcement body have a curved shape having no corner portion. Accordingly, it is possible to further reduce the stress concentration when the shaft is pulled at the distal end of the reinforcement body.

In the distal end portion of the reinforcement body, an intersection portion in which the wires overlap each other is disposed, and the wires overlapping each other in the intersection portion are fixed. Accordingly, it is possible to help prevent the distal ends of the wires from breaking through the intermediate outer layer when the shaft is pulled.

In the reinforcement body, metallic wires are embedded inside the outer layer, and the ratio of the thickness of the intermediate outer layer to twice the thickness of the wires is within the range of, for example, 1.8 to 2.4. Accordingly, it is possible to help prevent increase in the outer diameter of the shaft and the maneuverability in the blood vessel from being deteriorated while securing the thickness of the intermediate outer layer.

The distance between a distal end position of the intermediate outer layer and a distal end position of the reinforcement body is within the range, for example, of 1.0 mm to 2.0 mm. Accordingly, when the shaft is pulled, it is possible to suppress the deterioration in the pushability of the shaft while sufficiently securing the elongation length of the intermediate outer layer.

In accordance with an exemplary embodiment, the reinforcement body includes metallic wires woven at regular pitches into a mesh shape, and the distance between the distal end position of the intermediate outer layer and the distal end position of the reinforcement body is within the range, for example, of three to seven times the pitch of the reinforcement body. Accordingly, the length of the portion not having the reinforcement body of the intermediate outer layer can be set within the appropriate range.

In accordance with an exemplary embodiment, a catheter is disclosed comprising: an elongated tube shaped shaft, the elongated tube shaped shaft having an inner layer having a lumen along a longitudinal direction, an outer layer covering an outer peripheral side of the inner layer, and a reinforcement body disposed on the outer peripheral side of the inner layer; the outer layer having a distal outer layer on a distal end portion of the shaft, an intermediate outer layer proximal to the distal outer layer, and a proximal outer layer proximal to the intermediate outer layer; and wherein the intermediate outer layer is more flexible and thicker than the proximal outer layer, and a distal end of the reinforcement body is located proximal to a distal end of the intermediate outer layer.

In accordance with another exemplary embodiment, a catheter is disclosed comprising: an elongated tube shaped shaft, the elongated tube shaped shaft having an inner layer having a lumen along an axial direction, an outer layer covering an outer peripheral side of the inner layer, and a reinforcement body disposed on the outer peripheral side of the inner layer; the outer layer having a distal outer layer on a distal end portion of the shaft, an intermediate outer layer proximal to the distal outer layer, and a proximal outer layer proximal to the intermediate outer layer; a distance from an inner surface to an outer surface of the intermediate outer layer being greater than a distance form an inner surface to an outer surface of the proximal outer layer, and a distal end of the reinforcement body being located proximal to a distal end of the intermediate outer layer; and wherein the reinforcement body includes metallic wires woven into a mesh shape and embedded in the outer layer, and a ratio of a thickness of the intermediate outer layer to twice a thickness of the metallic wires being 1.8 to 2.4.

In accordance with a further exemplary embodiment, a catheter is disclosed comprising: an elongated tube shaped shaft, the elongated tube shaped shaft having an inner layer having a lumen along a longitudinal direction, an outer layer covering an outer peripheral side of the inner layer, and a reinforcement body comprised of wires woven into a mesh shape disposed on the outer peripheral side of the inner layer; the outer layer having a distal outer layer on a distal end portion of the shaft, an intermediate outer layer proximal to the distal outer layer, and a proximal outer layer proximal to the intermediate outer layer; the intermediate outer layer being more flexible and thicker than the proximal outer layer, and a distal end of the reinforcement body is located proximal to a distal end of the intermediate outer layer; and wherein distal end portions of the wires located at the distal end of the reinforcement body have a curved shape having no corner portion.

DETAILED DESCRIPTION

Hereinafter, an embodiment of the present disclosure will be described with reference to the drawings. Note that, for the convenience of description, there are cases where the dimensional ratios of the drawings are exaggerated and are different from the actual ratios. Note that, in the present specification, a side in which a catheter 10 is inserted into a biological lumen is referred to as a "distal end" or a "distal side", and a hand-side to be operated is referred to as a "proximal end" or a "proximal side".

Figure 1:
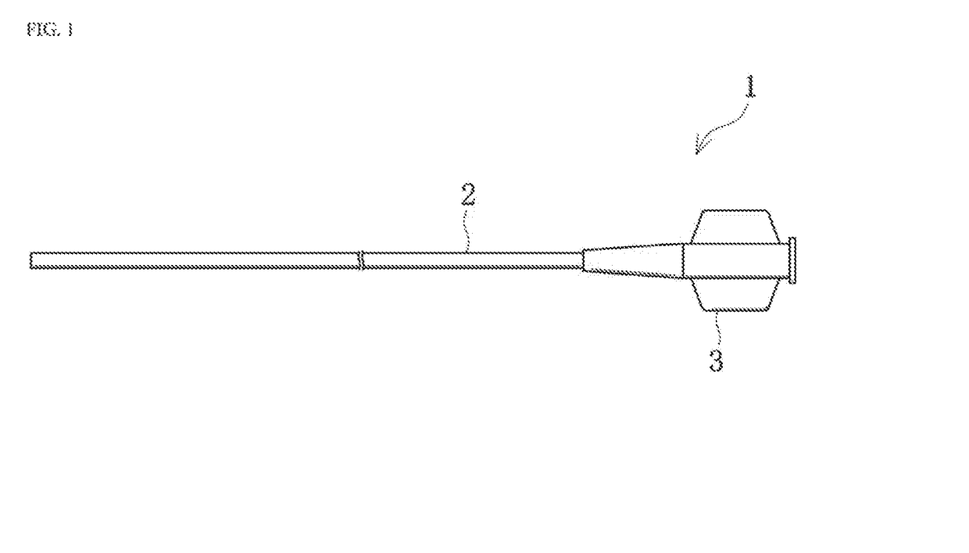
FIG. 1 is a front view of a catheter of an exemplary embodiment.

In accordance with an exemplary embodiment, the catheter 1 of the exemplary embodiment is a guiding catheter inserted from a blood vessel of an arm such as a radial artery to a vicinity of a target site such as a stenosed site of the blood vessel of a lower extremity. The guiding catheter can be used to introduce a treatment catheter such as a balloon catheter to a target site by inserting the treatment catheter inside of the guiding catheter. As shown in FIG. 1, the catheter 1 has a shaft 2, which is an elongated tube shaped body, and a hub 3 provided in a proximal end portion of the shaft 2.

Figure 2:
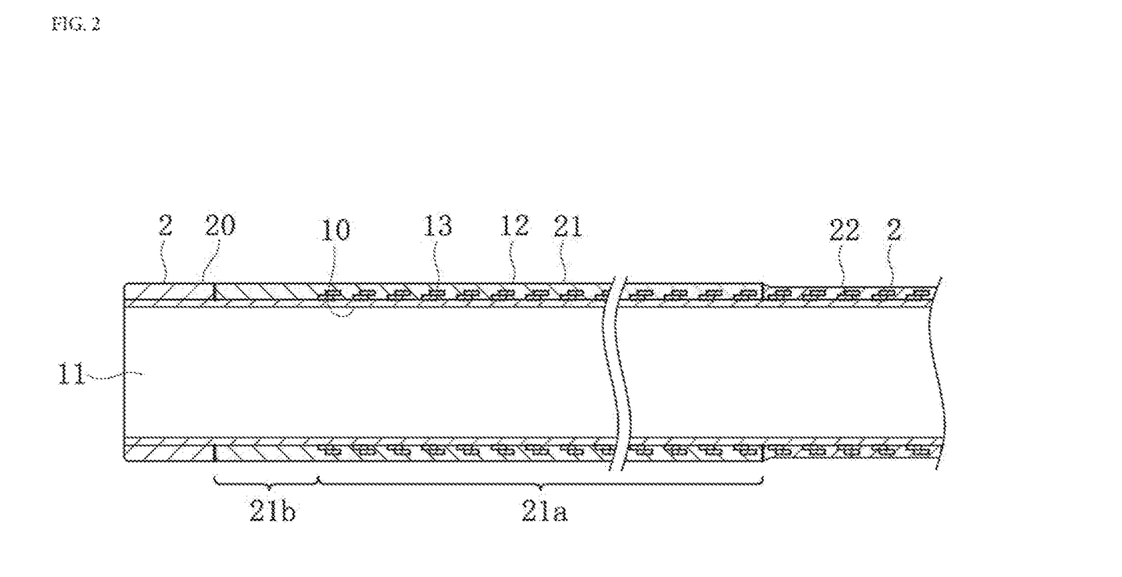
FIG. 2 is a cross-sectional view of a distal end portion of a shaft.

As shown in FIG. 2, the shaft 2 is a tube shaped body having a two-layer structure of an inner layer 10 having a lumen 11 along a longitudinal direction (i.e., length direction or axial direction) and an outer layer 12 covering an outer peripheral side of the inner layer 10. Moreover, the shaft 2 has a reinforcement body 13 between the inner layer 10 and the outer layer 12. The shaft 2 is formed of a flexible material. Therefore, the shaft 2 can be inserted along the shape of the blood vessel.

The material of the outer layer 12 can include, for example, thermoplastic elastomers such as a styrene-based elastomer, a polyolefin-based elastomer, a polyurethane-based elastomer, a polyester-based elastomer, a polyimide-based elastomer, a polybutadiene-based elastomer, a trans-polyisoprene-based elastomer, a fluororubber-based elastomer, and a chlorinated polyethylene-based elastomer. In accordance with an exemplary embodiment, one type or a combination of two or more types of these materials (polymer alloy, polymer blend, laminated body, and the like) can be used as the material of the outer layer 12.

In accordance with an exemplary embodiment, it can be desirable that the inner layer 10 is made of a material which has low friction in a portion contacting a medical instrument when the medical instrument such as the treatment catheter is inserted into the lumen 11. Accordingly, the medical instrument inserted into the shaft 2 can be moved in the length direction against smaller sliding friction, thereby improving operability. Examples of a low-friction material can include a fluorine-based resin such as polytetrafluoroethylene (PTFE).

Figure 3:
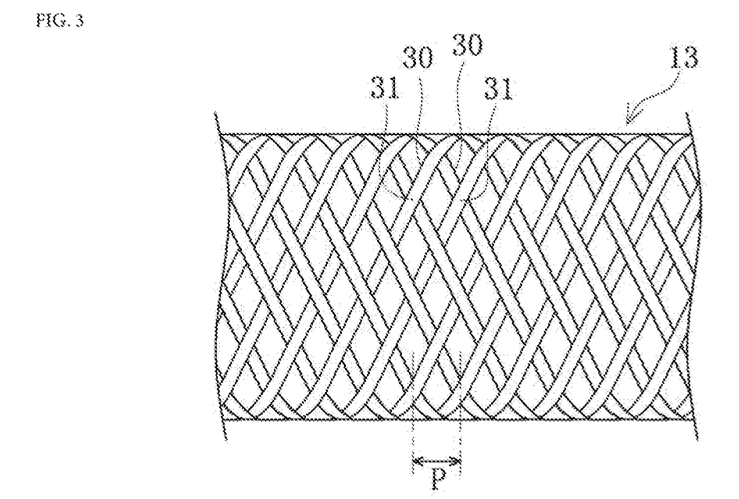
FIG. 3 is a partial front view of a reinforcement body.

In accordance with an exemplary embodiment, the reinforcement body 13 is provided to reinforce the shaft 2. As shown in FIG. 3, the reinforcement body 13 can include a plurality of wires 30 woven at regular pitches P (i.e., recurring at uniform intervals) into a mesh shape. Here, the pitch P refers to an axial distance between intersection portions 31 where the wires 30 intersect each other. A resin material of the outer layer 12 enters a gap between the plurality of wires 30 of the reinforcement body 13. The material of the wire 30 can be, for example, a metal such as stainless steel or NiTi (i.e., nickel titanium or Nitinol). The cross-sectional shape of the wire 30 is formed in a flat plate shape. Accordingly, the thickness of the reinforcement body 13 can be reduced. However, the cross-sectional shape of the wire 30 is not limited to this, and may be circular, elliptical, oval, or polygonal or the like. Moreover, the wire 30 may be made of a resin material.

In accordance with an exemplary embodiment, the outer layer 12 of the shaft 2 is further separated into three portions in the longitudinal direction (i.e., length direction or axial direction) of the shaft 2. The distal end portion of the shaft 2 is a distal outer layer 20. An intermediate outer layer 21 is provided more proximal than the distal outer layer 20. A proximal outer layer (or base outer layer) 22 is provided more proximal than the intermediate outer layer 21. In accordance with an exemplary embodiment, the intermediate outer layer 21 is formed of a material having more flexibility than the proximal outer layer 22. Moreover, the distal outer layer 20 is formed of a material having more flexibility than the intermediate outer layer 21. The hardness of the proximal outer layer 22 can be, for example, within the range of the shore D hardness 50 to 80, and more preferably in the range of the shore D hardness 60 to 70. The hardness of the intermediate outer layer 21 is within the range of the shore D hardness 35 to 50, and more preferably within the range of the shore D hardness 45 to 50. The hardness of the distal outer layer 20 can be, for example, within the range of the shore D hardness 30 to 50, and more preferably within the range of the shore D hardness 40 to 45.

In the outer layer 12, the intermediate outer layer 21 and the distal outer layer 20 are thicker than the proximal outer layer 22 (i.e., a distance from an inner surface to an outer surface of the intermediate outer layer 21 is greater than a distance form an inner surface to an outer surface of the proximal outer layer 22). In the region of the intermediate outer layer 21 and the distal outer layer 20, the cross-sectional area of the shaft 2 is constant (i.e., the same) along the length (or axial) direction.

In accordance with an exemplary embodiment, the distal outer layer 20 contains a substance having an X-ray radiopacity. In accordance with an alternative embodiment, the intermediate outer layer 21 does not have a radiopacity. Therefore, when the shaft 2 is inserted into the blood vessel, only the distal end portion of the shaft 2 can be imaged under the X-ray fluoroscopy to improve visibility.

The reinforcement body 13 is provided over from the proximal outer layer 22 to the intermediate outer layer 21 in the length direction of the shaft 2. Moreover, the distal end of the reinforcement body 13 is located more proximal than the distal end of the intermediate outer layer 21. Therefore, the intermediate outer layer 21 has a proximal side portion 21a which has the reinforcement body 13 and a distal side portion 21b which does not have the reinforcement body 13.

Figure 4:
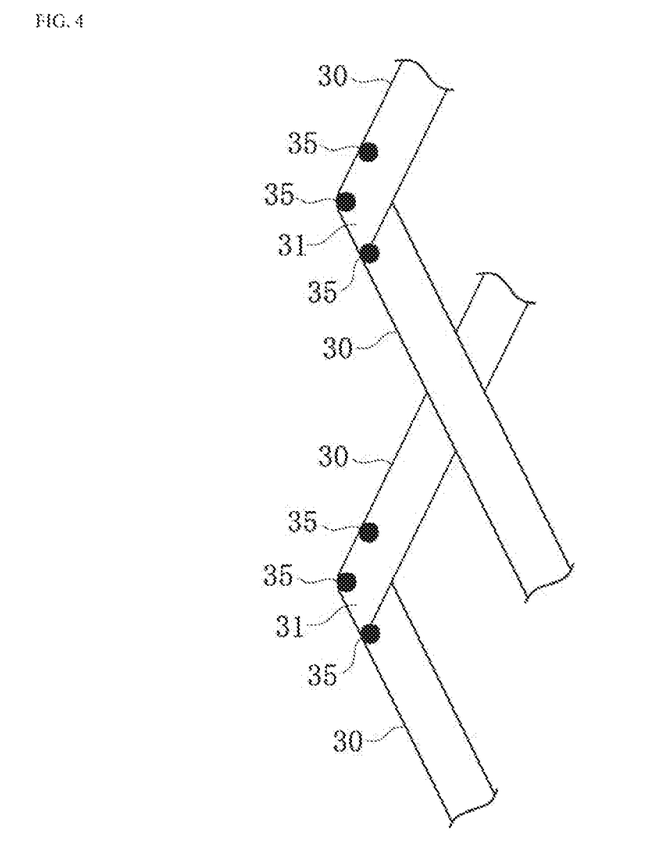
FIG. 4 is a partial enlarged front view of a distal end portion of the reinforcement body.

As shown in FIG. 4, the intersection portion 31 of wires 30 is disposed in the distal end portion of the reinforcement body 13. The intersection portion 31 has weld portions 35 in a portion that becomes both sides of the distal end portion of each of the two wires 30 overlapping each other. The two wires 30 overlapping each other in the intersection portion 31 of the distal end portion of the reinforcement body 13 are welded and bonded in the weld portions 35. In the weld portions 35 located at the distal ends of the intersection portion 31, the wires 30 have a curved shape having no corner in the end portion. The curved shape is formed when the wires 30 are bonded to each other.

Figure 5:
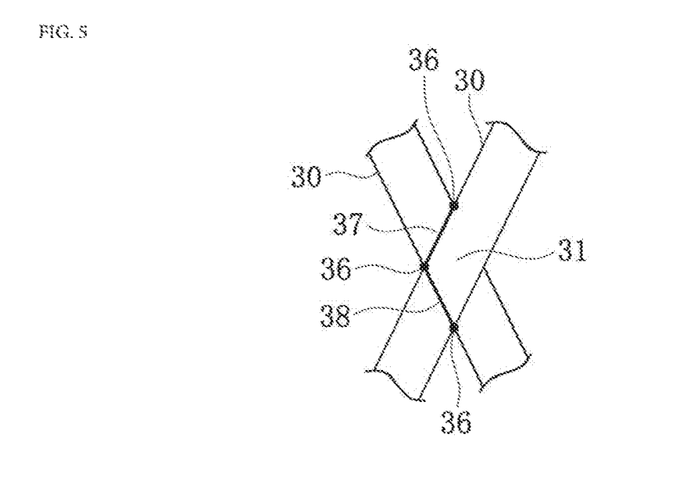
FIG. 5 is a partial enlarged front view of the reinforcement body in a state before a wire is cut.

In accordance with an exemplary embodiment, the distal end shape of the reinforcement body 13 shown in FIG. 4 is formed as follows. As shown in FIG. 5, in the intersection portion 31 where two wires 30 are overlapping each other, each of the wires 30 is laser cut at a first line 37 and a second line 38 respectively along the side of the other wire 30. At the same time, the wires 30 are welded and bonded to each other by laser welding at the first line 37 and the second line 38. At this time, a curved shape located at the distal end of the intersection portion 31 is formed. Moreover, a bulge shape is formed on a surface of the welded portion of the intersection portion 31.

Note that, as a method of bonding the wires 30 to each other, other methods such as resistance welding, soldering, brazing, or adhesion with an adhesive may be used in addition to the laser welding.

If the shaft 2 is pulled in the proximal direction in a case where the distal end portion of the shaft 2 is secured or firmly fixed in the blood vessel is or during the operation of removing the shaft 2 from the blood vessel, the shaft 2 is elongated by the tensile load. As described above, the intermediate outer layer 21 is flexible, and the proximal outer layer 22 has flexibility lower than the intermediate outer layer 21. Therefore, when elongating the shaft 2, first, a portion of the intermediate outer layer 21, which has relatively high flexibility and small yield point load is elongated. Next, a portion of the proximal outer layer 22 is elongated.

When the portion of the proximal outer layer 22 starts to be elongated, the tensile load applied to the distal end portion of the shaft 2 increases. When the tensile load is increased, the breaking occurs in the region of the intermediate outer layer 21. In the present embodiment, the intermediate outer layer 21 is thicker than the proximal outer layer 22 in the shaft 2, so that the breaking strength against the tensile load of the shaft 2 can be increased.

In accordance with an exemplary embodiment, the intersection portion 31 is disposed as described above in the distal end portion of the reinforcement body 13. When bonding the wires 30 in the intersection portion 31 together, a bulge shape is formed in the intersection portion 31, and the wall thickness of the intersection portion is larger than other portions. In contrast, when the intermediate outer layer 21 is thicker than the proximal outer layer 22, the distal end portion of the reinforcement body 13 can be prevented from being exposed on the outer surface of the intermediate outer layer 21. When the reinforcement body 13 is exposed on the outer surface of the intermediate outer layer 21, stress concentration occurs in that portion during pulling of the shaft 2, and thereby the breaking strength of the shaft 2 can be reduced. Since the distal end portion of the reinforcement body 13 can be prevented from being exposed on the outer surface of the intermediate outer layer 21 in the present embodiment, the breaking strength against the tensile load of the shaft 2 can be increased. A certain thickness is required between a bulge shaped surface of the reinforcement body 13 and a surface of the intermediate outer layer 21. In accordance with an exemplary embodiment, when the thickness of the intermediate outer layer 21 is too thick, the outer diameter of the shaft 2 is increased so that the maneuverability in the blood vessel is reduced. Therefore, the thickness of the intermediate outer layer 21 is required to be set within an appropriate range. The appropriate thickness range of the intermediate outer layer 21 will be described later.

In a case where the shaft 2 is pulled, the stress concentration can occur at the distal end of the reinforcement body 13, so that the breaking tends to occur in this position. If the reinforcement body 13 is provided up to the distal end of the intermediate outer layer 21, the stress concentration occurs at the vicinity of the boundary between the intermediate outer layer 21 and the distal outer layer 20, such that the vicinity of the boundary between the intermediate outer layer 21 and the distal outer layer 20 tends to break more easily. In the present embodiment, the distal end of the reinforcement body 13 is located more proximal than the distal end of the intermediate outer layer 21. That is, since the intermediate outer layer 21 has the distal side portion 21b which does not have the reinforcement body 13, the breakage in the vicinity of the boundary between the intermediate outer layer 21 and the distal outer layer 20 can be suppressed.

When the intermediate outer layer 21 does not have the distal side portion 21b or the distal side portion 21b of the intermediate outer layer 21 is too short, the yield elongation length in the portion of the intermediate outer layer 21 is reduced when the shaft 2 is pulled. In this case, the elongation of the portion of the proximal outer layer 22 starts early, and the tensile load applied to the distal end portion of the reinforcement body 13 increases early. Therefore, the shaft 2 tends to break in a position at the vicinity of the distal end portion of the reinforcement body 13. In contrast, when the distal side portion 21b is provided with a length equal to or more than a certain length, the yield elongation length of the portion of the intermediate outer layer 21 increases, such that breakage of shaft 2 in a position at the vicinity of the distal end portion of the reinforcement body 13 can be suppressed. In accordance with an exemplary embodiment, when the length of the distal side portion 21b is too long, the length of the portion that does not have the reinforcement body 13 increases in the distal end portion of the shaft 2. For this, the pushability of the shaft 2 can be reduced, and the operability of the catheter 1 can be reduced. Therefore, the length of the distal side portion 21b can be required to be set within an appropriate range. The appropriate range of the length of the distal side portion 21b will be described later.

Moreover, by providing the distal side portion 21b which does not have the reinforcement body 13 in the intermediate outer layer 21, the sliding friction of the medical instrument passing through the lumen 11 of the shaft 2 can be reduced. In the TRI technique, an operator inserts a balloon catheter into the lumen 11 of the shaft 2, and inflates the balloon at a target site in the blood vessel. Thereafter, the operator deflates the balloon to remove the balloon catheter through the shaft 2. At the time of removal, the outer diameter of the balloon can be slightly larger than at the time of insertion. Therefore, at the time of removing the balloon catheter, the sliding friction of the balloon against the distal end portion of the shaft 2 increases. Since the catheter 1 of the present embodiment has the distal side portion 21b which does not have the reinforcement body 13 in the intermediate outer layer 21, when the balloon passes through the distal end portion of the shaft 2, the distal side portion 21b tends to be widened in the circumferential direction. Therefore, with the catheter 1 of the present embodiment, the sliding friction at the time of removing the balloon catheter can be reduced.

Moreover, in the catheter 1 of the present embodiment, since the intermediate outer layer 21 has the distal side portion 21b which does not have the reinforcement body 13, the distance from the distal end of the shaft 2 to the distal end of the reinforcement body 13 is relatively large. Therefore, the spread of the inner diameter from the proximal side of the shaft 2 toward the distal side is milder (i.e., less than) compared to the case where the distal end of the reinforcement body 13 is located near the distal end portion of the shaft 2. Therefore, the catheter 1 of the present embodiment can reduce the load against the distal end portion of the shaft 2 and the distal end portion of the reinforcement body 13.

When a single wire 30 is disposed in the end portion of the reinforcement body 13, the wire 30 tends to break through the intermediate outer layer 21 and to be exposed on the outer surface of the shaft 2. In the catheter 1 of the present embodiment, the intersection portion 31 in which the wires 30 are bonded to each other is disposed in the distal end portion of the reinforcement body 13, such that the possibility of wire 30 breaking through the intermediate outer layer 21 and to be exposed on the outer surface of the shaft 2 can be reduced. Moreover, since the distal end of the intersection portion 31 is formed into a curved shape having no corner, when the tensile load is applied to the shaft 2, the stress concentration at the distal end of the reinforcement body 13 is relieved, and the breaking of the shaft 2 can be suppressed.

Moreover, the wires 30 forming the reinforcement body 13 are fixed only in the intersection portion 31 of the distal end portion. Such a reinforcement body 13 is more likely to be elastically deformed also on the side more proximal than the distal end portion as compared to the case where the wires 30 are fixed to each other. Therefore, when a site having a large outer diameter such as the balloon after being inflated and deflated once passes through the inside of the shaft 2 in the medical instrument, the inner diameter tends to spread in the distal end portion of the shaft 2, and the maneuverability of the medical instrument can be improved.

The catheter 1 of the present embodiment has the inner layer 10, which is continuous over the proximal outer layer 22, the intermediate outer layer 21, and the distal outer layer 20. Therefore, at the time of removing a medical instrument such as a balloon catheter, the distal end portion of the shaft 2 can be prevented from being caught in the lumen 11 of the shaft 2 by reducing the sliding friction of the distal end portion of the shaft 2.

In the present embodiment, the wall thickness of the distal outer layer 20 is the same as that of the intermediate outer layer 21. Therefore, the distal outer layer 20 is relatively thick-walled such that the distal outer layer 20 helps prevent the distal end portion of the shaft 2 from being caught in the lumen 11 of the shaft 2. The wall thickness of the distal outer layer 20 may be smaller or larger than the wall thickness of the intermediate outer layer 21, but it is desirable to be thick-walled as in the present embodiment.

Figure 6:
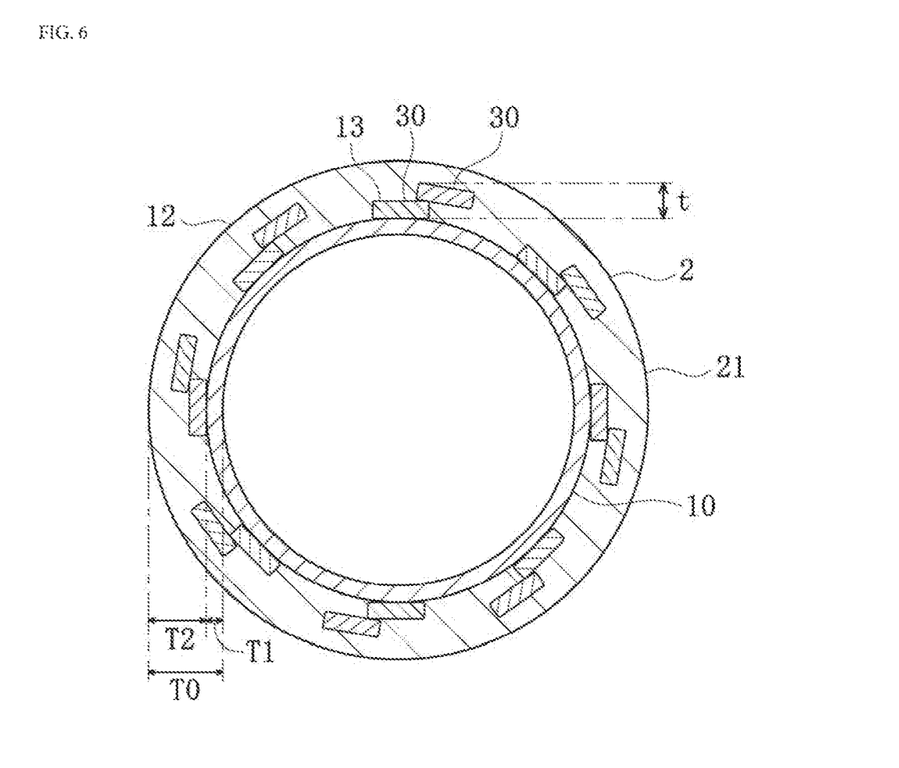
FIG. 6 is a cross-sectional view of the shaft in a region of an intermediate outer layer.

As shown in FIG. 6, the wall thickness of the shaft 2 in the portion of the intermediate outer layer 21, the wall thickness of the inner layer 10, and the wall thickness of the intermediate outer layer 21 are referred to as T0, T1, and T2, respectively. Moreover, the thickness of the portion where the wires 30 of the reinforcement body 13 are overlapped is referred to as t. The portion where the wires 30 of the reinforcement body 13 are overlapped is the intersection portion 31 where the wires 30 intersect in FIG. 3. In accordance with an exemplary embodiment, the ratio T2/t of the wall the thickness T2 of the intermediate outer layer 21 to the thickness t of the reinforcement body 13 is referred to as a wall thickness ratio r. Moreover, the axial length of the distal side portion 21b which does not have the reinforcement body 13 of the intermediate outer layer 21 is referred to as L.

Figure 7:
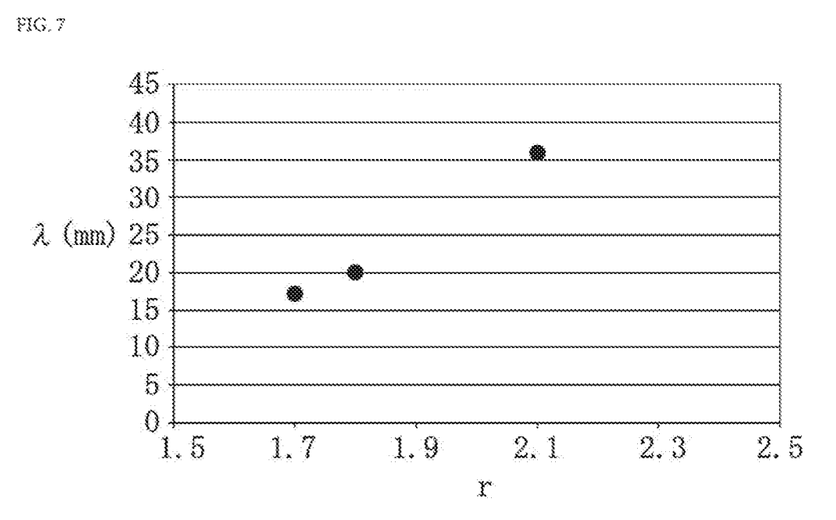
FIG. 7 is a graph showing a relationship between a breaking elongation length λ and a wall thickness ratio r.

The applicant manufactured a plurality of shafts 2 having different wall thicknesses of the intermediate outer layer 21, and measured the tensile strength and breaking elongation length $\lambda$ of the plurality of shafts 2 having different wall thicknesses of the intermediate outer layer 21. Three kinds of shafts 2 having different wall thicknesses of the intermediate outer layer 21 were prepared. The conditions of the inner diameter and the wall thickness T1 of the inner layer 10 of each of the shafts 2 are the same. Moreover, in the shafts 2, the outer diameter of the region of the proximal outer layer 22 is 2.37 mm. The dimensions and measurement results of the shafts 2 of the conditions are shown in Table 1, and the relationship between the breaking elongation length $\lambda$ and the wall thickness ratio r is shown in FIG. 7, respectively.

TABLE 1

|  | Condition 1-1 | Condition 1-2 | Condition 1-3 |
|---|---|---|---|
| Outer diameter (mm) | 2.39 | 2.40 | 2.43 |
| Inner diameter (mm) | 2.20 | 2.20 | 2.20 |
| Shaft wall thickness T0 (mm) | 0.095 | 0.100 | 0.115 |
| Inner layer wall thickness T1 (mm) | 0.01 | 0.01 | 0.01 |
| Intermediate outer layer wall thickness T2 (mm) | 0.085 | 0.090 | 0.105 |
| Reinforcement body thickness t (mm) | 0.050 | 0.050 | 0.050 |
| Wall thickness ratio r | 1.7 | 1.8 | 2.1 |
| Tensile strength (gf) | 980 | 1191 | 1292 |
| Breaking elongation length (mm) | 17.0 | 19.6 | 36.0 |

According to the result, it was found that the larger the wall thickness ratio r, which is the ratio of the wall the thickness T2 of the intermediate outer layer 21 to the thickness t of the reinforcement body 13, the greater tensile strength and breaking elongation length. Since the tensile strength of the shaft 2 is required to be 1,000 gf or more, Condition 1-1 does not satisfy the requirement. Therefore, in accordance with an exemplary embodiment, the lower limit value of the wall thickness ratio r is 1.8. In a case where the wall thickness ratio r is larger than 2.4, the outer diameter of the shaft 2 is larger than 2.46 mm. In this case, it exceeds the maximum value of the required outer diameter, and the distal end portion of the shaft 2 becomes hard so that the operability of the catheter 1 is deteriorated. Therefore, in accordance with an exemplary embodiment, the upper limit value of the wall thickness ratio r is 2.4. From the above, it is preferable that the wall thickness ratio r set within the range of, for example, 1.8 to 2.4.

The thickness obtained by subtracting the thickness t of the reinforcement body 13 from the wall thickness T2 of the intermediate outer layer 21 corresponds to the thickness between the surface of the reinforcement body 13 and the surface of the shaft 2. When the range of the wall thickness ratio r is 1.8 to 2.4, the thickness between the surface of the reinforcement body 13 and the surface of the shaft 2 is 0.04 to 0.07 mm. The thickness needs to be 0.02 mm or more. In the intersection portion 31 disposed at the distal end of the reinforcement body 13, a bulge shape by bonding is formed as described above. Even in the consideration of the height of the bulge shape, if the wall thickness ratio r is set within the range of 1.8 to 2.4, it is possible to secure the thickness between the surface of the reinforcement body 13 and the surface of the shaft 2 to be, for example, 0.02 mm or more.

Figure 8:
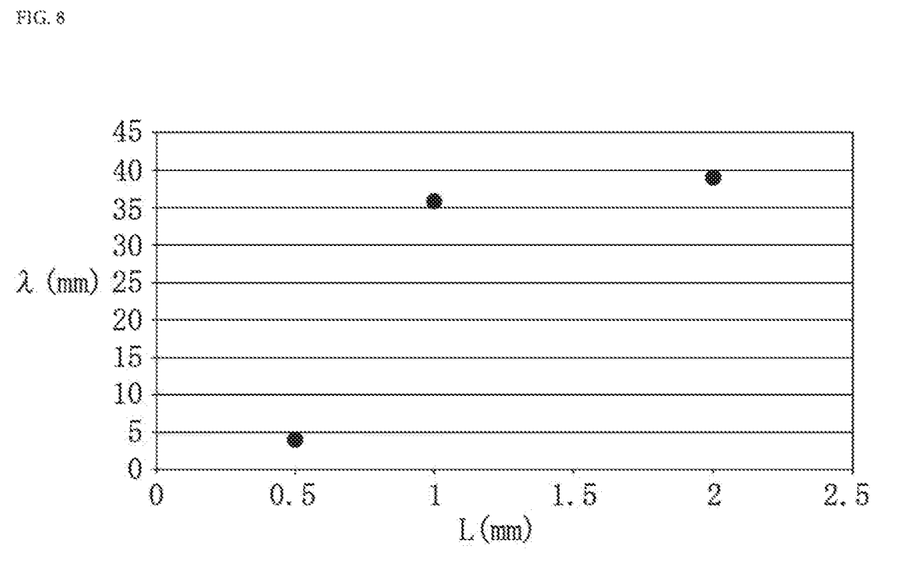
FIG. 8 is a graph showing a relationship between the breaking elongation length λ and a length L of a distal side portion of shaft.

Moreover, the applicant manufactured a plurality of shafts 2 having different lengths L of the distal side portion 21b, and measured the tensile strength and the breaking elongation length λ of the plurality of shafts 2 having lengths L of the distal side portion 21b. Three kinds of shafts 2 having different lengths L of the distal side portion 21b were prepared. The conditions of the outer diameter, the inner diameter, and the inner layer wall thickness of each of the shafts 2 are the same. Moreover, in the shafts 2, the outer diameter of the region of the proximal outer layer 22 is 2.37 mm. The dimensions and measurement results of the shafts 2 of the conditions are shown in Table 2, and the relationship between the breaking elongation length λ and the length L of the distal side portion 21b is shown in FIG. 8, respectively. Note that, Condition 2-2 is under the same condition as Condition 1-3.

TABLE 2

|  | Condition 2-1 | Condition 2-2 | Condition 2-3 |
|---|---|---|---|
| Outer diameter (mm) | 2.43 | 2.43 | 2.43 |
| Inner diameter (mm) | 2.20 | 2.20 | 2.20 |
| Shaft wall thickness T0 (mm) | 0.115 | 0.115 | 0.115 |
| Inner layer wall thickness T1 (mm) | 0.01 | 0.01 | 0.01 |
| Intermediate outer layer wall thickness T2 (mm) | 0.105 | 0.105 | 0.105 |
| Reinforcement body thickness t (mm) | 0.050 | 0.050 | 0.050 |
| Distal side portion length L (mm) | 0.5 | 1.0 | 2.0 |
| Tensile strength (gf) | 910 | 1292 | 1288 |
| Breaking elongation length (mm) | 3.58 | 36.0 | 39.0 |

According to the result, the length L of the distal side portion 21b is desirable to be within the range of, for example, 1.0 to 2.0 mm. Moreover, the pitch P of the reinforcement body 13 is within the range of, for example, 0.27 to 0.42 mm. Therefore, the length L of the distal side portion 21b is set within the range of, for example, three to seven times the pitch P of the reinforcement body 13, more preferably to the range of, for example, three to five times.

As described above, the catheter 1 according to the present embodiment includes the elongated tube shaped shaft 2. The shaft 2 has the inner layer 10 having the lumen 11 along the longitudinal or axial direction, the outer layer 12 covering the outer peripheral side of the inner layer 10, and the reinforcement body 13 disposed on the outer peripheral side of the inner layer 10. The outer layer 12 has the distal outer layer 20 of the distal end portion of the shaft 2, the intermediate outer layer 21 is proximal to the distal outer layer 20, and the proximal outer layer (or base outer layer) 22 is proximal to the intermediate outer layer 21. The intermediate outer layer 21 is more flexible and thicker than the proximal outer layer (or base outer layer) 22, and the distal end of the reinforcement body 13 is located more proximal than the distal end of the intermediate outer layer 21. With the catheter 1, the breaking strength of the distal end portion of the flexible shaft 2 can be increased while suppressing the occurrence of the stress concentration at the distal end of the reinforcement body 13 when the shaft 2 is pulled.

Moreover, the reinforcement body 13 includes metallic wires 30 woven into a mesh shape, and the distal end portions of the wires 30 located at the distal end of the reinforcement body 13 have a curved shape having no corner portion. Accordingly, the stress concentration when the shaft 2 is pulled at the distal end of the reinforcement body 13 can be further reduced.

Moreover, in the distal end portion of the reinforcement body 13, the intersection portion 31 in which the wires 30 overlap each other is disposed, and the wires 30 overlapping each other in the intersection portion 31 are fixed. Accordingly, the distal ends of the wires 30 can be prevented from breaking through the intermediate outer layer 21 when the shaft 2 is pulled.

Moreover, in the reinforcement body 13, the metallic wires 30 are embedded inside the outer layer 12, and the ratio of the thickness of the intermediate outer layer 21 to twice the thickness of the wires 30 is within the range of, for example, 1.8 to 2.4. Accordingly, it is possible to prevent the increase in the outer diameter of the shaft 2 and the maneuverability in the blood vessel from being deteriorated while securing the thickness of the intermediate outer layer 21.

Moreover, the distance between the distal end position of the intermediate outer layer 21 and the distal end position of the reinforcement body 13 is within the range of, for example, 1.0 to 2.0 mm. Accordingly, when the shaft 2 is pulled, it is possible to suppress the deterioration in the pushability of the shaft 2 while sufficiently securing the elongation length of the intermediate outer layer 21.

Moreover, the reinforcement body 13 includes metallic wires 30 woven at regular pitches into a mesh shape, and the distance between the distal end position of the intermediate outer layer 21 and the distal end position of the reinforcement body 13 is within the range of three to seven times the pitch of the reinforcement body 13. Accordingly, the length of the portion not having the reinforcement body 13 of the intermediate outer layer 21 can be set within the appropriate range.

The detailed description above describes a catheter to be inserted into a biological lumen. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A catheter comprising:
   an elongated tube shaped shaft, the elongated tube shaped shaft having an inner layer having a lumen along a longitudinal direction, an outer layer covering an outer peripheral side of the inner layer, and a reinforcement body disposed on the outer peripheral side of the inner layer;
   the outer layer including a distal outer layer on a distal end portion of the shaft, an intermediate outer layer proximal to the distal outer layer, and a proximal outer layer proximal to the intermediate outer layer, each of the distal outer layer, the intermediate outer layer, and the proximal outer layer covering the outer peripheral side of the inner layer; and
   wherein the intermediate outer layer is more flexible than the proximal outer layer and a distance from an inner surface to an outer surface of the intermediate outer layer is greater than a distance from an inner surface to an outer surface of the proximal outer layer, and a distal end of the reinforcement body is located proximal to a distal end of the intermediate outer layer.

2. The catheter according to claim 1, wherein the reinforcement body comprises metallic wires woven into a mesh shape.

3. The catheter according to claim 2, wherein distal end portions of the wires located at a distal end of the reinforcement body have a curved shape.

4. The catheter according to claim 2, wherein, in a distal end portion of the reinforcement body, an intersection portion in which the wires overlap each other is disposed, and the wires overlapping each other in the intersection portion are fixed.

5. The catheter according to claim 1, wherein, in the reinforcement body, metallic wires are embedded inside the outer layer, and a ratio of a thickness of the intermediate outer layer to twice a thickness of the wires is 1.8 to 2.4.

6. The catheter according to claim 1, wherein a distance between a distal end position of the intermediate outer layer and a distal end position of the reinforcement body is 1.0 mm to 2.0 mm.

7. The catheter according to claim 1, wherein the reinforcement body comprises metallic wires woven at regular pitches into a mesh shape, and a distance between a distal end position of the intermediate outer layer and a distal end position of the reinforcement body is three to seven times a pitch of the reinforcement body.

8. The catheter according to claim 1, comprising:
   the proximal outer layer having a shore D hardness of 50 to 80;
   the intermediate outer layer having a shore D hardness of 35 to 50; and
   the distal outer layer having a shore D hardness 30 to 50.

9. The catheter according to claim 1, wherein a distal portion of the intermediate outer layer does not include the reinforcement layer, and the inner layer extends to a distal end of the catheter.

10. The catheter according to claim 1, wherein the distal outer layer contains a substance having an X-ray radiopacity.

11. A catheter comprising:
    an elongated tube shaped shaft, the elongated tube shaped shaft having an inner layer having a lumen along an axial direction, an outer layer covering an outer peripheral side of the inner layer, and a reinforcement body disposed on the outer peripheral side of the inner layer;
    the outer layer having a distal outer layer on a distal end portion of the shaft, an intermediate outer layer proximal to the distal outer layer, and a proximal outer layer proximal to the intermediate outer layer, each of the distal outer layer, the intermediate outer layer, and the proximal outer layer covering the outer peripheral side of the inner layer;
    a distance from an inner surface to an outer surface of the intermediate outer layer being greater than a distance form an inner surface to an outer surface of the proximal outer layer, and a distal end of the reinforcement body being located proximal to a distal end of the intermediate outer layer; and
    wherein the reinforcement body includes metallic wires woven into a mesh shape and embedded in the outer layer, and a ratio of a thickness of the intermediate outer layer to twice a thickness of the metallic wires being 1.8 to 2.4.

12. The catheter according to claim 11, wherein distal end portions of the wires located at the distal end of the reinforcement body have a curved shape.

13. The catheter according to claim 12, wherein, in a distal end portion of the reinforcement body, an intersection portion in which the wires overlap each other is disposed, and the wires overlapping each other in the intersection portion are fixed.

14. The catheter according to claim 11, wherein a distance between a distal end position of the intermediate outer layer and a distal end position of the reinforcement body is 1.0 mm to 2.0 mm; and
    wherein the reinforcement body comprises metallic wires woven at regular pitches into a mesh shape, and a distance between a distal end position of the intermediate outer layer and a distal end position of the reinforcement body is three to seven times a pitch of the reinforcement body.

15. The catheter according to claim 11, wherein a distal portion of the intermediate outer layer does not include the reinforcement layer, and the inner layer extends to a distal end of the catheter.

16. The catheter according to claim 11, wherein the distal outer layer contains a substance having an X-ray radiopacity.

17. A catheter comprising:
    an elongated tube shaped shaft, the elongated tube shaped shaft having an inner layer having a lumen along a longitudinal direction, an outer layer covering an outer peripheral side of the inner layer, and a reinforcement body comprised of wires woven into a mesh shape disposed on the outer peripheral side of the inner layer;

the outer layer including a distal outer layer on a distal end portion of the shaft, an intermediate outer layer proximal to the distal outer layer, and a proximal outer layer proximal to the intermediate outer layer, each of the distal outer layer, the intermediate outer layer, and the proximal outer layer covering the outer peripheral side of the inner layer;

the intermediate outer layer being more flexible than the proximal outer layer and a distance from an inner surface to an outer surface of the intermediate outer layer is greater than a distance from an inner surface to an outer surface, and a distal end of the reinforcement body is located proximal to a distal end of the intermediate outer layer; and wherein distal end portions of the wires located at the distal end of the reinforcement body have a curved shape.

18. The catheter according to claim 17, wherein, in a distal end portion of the reinforcement body, an intersection portion in which the wires overlap each other is disposed, and the wires overlapping each other in the intersection portion are fixed.

19. The catheter according to claim 17, comprising:

a ratio of a thickness of the intermediate outer layer to twice a thickness of the wires being 1.8 to 2.4.

20. The catheter according to claim 17, wherein a distance between a distal end position of the intermediate outer layer and a distal end position of the reinforcement body is 1.0 mm to 2.0 mm.

* * * * *